United States Patent [19]

Kötzsch et al.

[11] Patent Number: 4,677,215

[45] Date of Patent: Jun. 30, 1987

[54] METHOD OF PREPARING PARTIALLY ESTERIFIED SILICON HALIDES

[75] Inventors: Hans-Joachim Kötzsch, Rheinfelden; Hans-Joachim Vahlensieck, Wehr, both of Fed. Rep. of Germany

[73] Assignee: Dynamit Nobel AG, Troisdorf Bez Cologne, Fed. Rep. of Germany

[21] Appl. No.: 891,215

[22] Filed: Jul. 28, 1986

[30] Foreign Application Priority Data

Jul. 31, 1985 [DE] Fed. Rep. of Germany ....... 3527437

[51] Int. Cl.$^4$ ................................................ C07F 7/18
[52] U.S. Cl. .................................................... 556/469
[58] Field of Search ......................................... 556/469

[56] References Cited

U.S. PATENT DOCUMENTS 2,474,704  6/1949  Thayer ............................ 556/469 X
2,626,273  1/1953  Hunter et al. ...................... 556/469
3,362,978  1/1968  Kanner ............................ 556/469 X
3,399,222  8/1968  Weyenberg ........................ 556/469
3,445,200  5/1969  Dunogues et al. ................ 556/469 X
4,016,188  4/1977  Kötzsch et al. .................... 556/469

Primary Examiner—Paul F. Shaver
Attorney, Agent, or Firm—Felfe & Lynch

[57] ABSTRACT

Disclosed is a method for the production of silicon ester halides by the equilibration of chlorosilanes and silane esters. Organic phosphorous compounds are used as catalysts. These catalysts make it possible to obtain a virtually pure end product with a defined partial ester structure, and they reduce the formation of undesired by-products. The final distillation can also be performed in the presence of these catalysts without the occurrence of any disproportioning destruction of the reaction products.

19 Claims, No Drawings

METHOD OF PREPARING PARTIALLY ESTERIFIED SILICON HALIDES

BACKGROUND OF THE INVENTION

The subject matter of the invention is a catalytically operating method for the production of organosilicic ester compounds of the general formula I, $$R_a SiX_n(OR')_{4-a-n} \quad (I)$$

which contain 1 to 3 halide moieties X in addition to alkoxy groups (OR') (n=1 to 3) and (4−a−n)≧1, and also, in some cases, a maximum of 2 substituents R (a=0 or 1 or 2) which can be hydrogen, alkyl groups (substituted with halogen if desired), alkenyl groups and/or aryl groups (substituted with halogen and/or alkyl). The ester groups —OR' are formed from primary or secondary alcohol moieties whose organic grouping R' consists in each case of a saturated and/or unsaturated, in some cases branched, alkyl group having 1 to 8 carbon atoms, which if desired can also contain ether oxygen functions. The partial esters of formula I obtained according to the claimed method therefore contain at least one R'O moiety, so that the sum of a +n can assumes values of 1, 2 or a maximum of 3. Formerly, these partial esters were made exclusively by esterifying chlorosilanes with less than stoichiometric amounts of alcohols. In this method, whenever monoesters were the object, considerable excesses of chlorosilanes had to be used in order to suppress insofar as possible the rate of formation of the undesired but unavoidably formed higher esterification stages. Nevertheless, even when the starting chlorosilane is in a three-fold to four-fold excess, it is not possible to achieve a monoester-to-diester ratio better than 2:1 to 3:1 (cf., e.g., K. A. Andrianov et al., J. Gen. Chem. USSR 26, 207 to 209, 1956; also Zhur. Obsh, Khim 20, 3754 to 3757, 1959; also USSR-Pat. No. 130891). The situation is still more complicated in the case of the production of diesters or triesters on account of the additional occurrence of other undesired stages of esterification. The disadvantages of this conventional procedure lie mainly in the exacting measures to be taken in distilling the pure product, and particularly in the excessively low yields of the desired degree of esterification. Attempts have therefore also been made to equilibrate esters of the general formula $$R_a Si(OR')_{4-a}$$

with chlorosilanes in the presence of hydrogen chloride (cf. Brit. Pat. No. 653,238; M. Kumada, J. Inst. Polytechn. Osaka Univ., Ser. C, 2, 139 to 146, 1952), but only the same disadvantageous results as referred to above were achieved. In addition a beside reaction takes place forming ethers (R'OR') and polysiloxanes followed by beccoming instable and by complete destruction of the product. Therefore this process is not in large scale application. Esterification experiments using pyridine as acid accept or have delivered the target product to a greater degree, but with still unsatisfactory yields. The special disadvantage of this method is the unavoidable production of undesired pyridine hydrochloride in a large amount, resulting in high costs (cf. U.S. Pat. No. 2,927,938).

Accordingly, for the better utilization of the starting substances, the problem existed of finding a method of production suitable for technical application, according to which the desired compounds of the general formula I will be obtained in a very direct manner, and the yield of by-products will be very low, and in which even mixtures of halogen silane partial esters can be used as starting products for the production and separation of a defined partial ester to a predominant degree.

THE INVENTION

This problem has been solved by the discovery of the method of the present invention.

In the invention a partial ester of formula I is formed in which the number of halogen and alkoxy groups is the same as the sum of the halogen and alkoxy groups of the starting products. The starting products are accordingly used in such a ratio to one another that the sum of their halogen and alkoxy groups corresponds to the halogen and alkoxy groups of the target product. An excess of one or the other starting product is possible; according to the invention, the excess then does not react to form the desired target product, and it has to be separated by distillation.

It also suffices to introduce ester groups in situ, in the presence of the catalysts according to the invention, by treating chlorosilanes with a corresponding equivalent number of R'OH, in which case halogen hydride in gas form has to be removed by the conventional methods used in the esterification of halogen silane. By the selective, balancing action of the catalysts according to the invention, the desired partial esters of general formula I are also produced in this case.

Products of the general formula I prepared by the method according to the invention are, for example, trichloroethoxysilane and trichloro-(2-ethyl)hexoxysilane, dichlorodiethoxysilane, dichlorodiisopropoxysilane, dichlorodi-secondary-butoxysilane, dichlorodi-(1-methoxy)isopropoxysilane, chloro-trimethoxysilane, chlorotriethoxysilane, chlorotriisopropoxy, -tri-secondary-butoxysilane, chlorotri-(1-methoxy)isopropoxysilane, methylethoxydichlorosilane, ethyldiethoxychlorosilane, methyldi-n-propoxychlorosilane, methyldiisobutoxychlorosilane, propyldiisopropoxychlorosilane, propyl-di-secondary-butoxychlorosilane, isobutylmethoxydichlorosilane, isobutylethoxydichlorosilane, isobutyldiisopropoxychlorosilane, isobutyldi-secondary-butoxychlorosilane, isobutyldi-(1-methoxy)isopropoxy-chlorosilane, octylmethoxydichlorosilane, hydrogenmethoxy-dichlorosilane, hydrogen diethoxychlorosilane, hydrogen diisobutoxychlorosilane, chloromethyl-(2-ethyl)hexoxydichlorosilane, 3-chloropropyldiisopropoxychlorosilane, vinyl ethoxydichlorosilane, vinyl di-n-butoxychlorosilane, allyldi-secondary-butoxychlorosilane, allyldi-(1-methoxy)isopropoxychlorosilane, phenyldiethoxychlorosilane, phenyldiisopropoxychlorosilane, p-, m- and o-bromophenyldimethoxychlorosilane, dimethylethoxychlorosilane, methylethylisobutoxychlorosilane, methylpropyl-(1-methoxy)isopropoxychlorosilane, methylisobutylisopropoxychlorosilane, methyl hydrogen-secondary-butoxychlorosilane, chloromethylmethyl-(1-methoxy)isopropoxychlorosilane, 3-chloropropylmethylmethoxychlorosilane, vinylmethylethoxychlorosilane, phenylmethyl-(1-methoxy)isopropoxychlorosilane, etc.

The practical application of the method of the invention is performed by mixing the above starting compounds, in the X:OR' ratio desired in the end product of structure I, with the catalyst to form a homogeneous solution. The catalyst concentration is to amount in this case to at least $10^{-5}$ wt. % of the weight of the total mixture up to 10 wt. %. Higher rates are possible but not necessary. The equilibration that immediately commences is a time reaction whose rate can be influenced by the selection of the temperature and of the catalyst. As a rule, a relatively slow equilibration reaction is observed at room temperatures, e.g., a reaction time of 20 to 30 hours, so that the choice of an elevated reaction temperature, e.g., the warming of the reaction mixture up to a few degrees below its boiling point, allows the advantage, according to the invention, of shorter equilibration times.

The work-up is performed by distillation after equilibration is complete. In working up the product by distillation with the catalysts according to the invention—which remain in the distillation residue—it is surprising that no reverse reactions occur in the sense of disproportionation to, for example, the starting products. The disadvantageous effect of such possible reverse reactions was, however, encountered in experiments performed with catalytic amounts of vanadium and zirconium esters, esters of phosphoric acid and orthophosphorus acid as well as a few nitrogen compounds (amine hydrochlorides and amides).

A special embodiment of the method of the invention sets out from chlorosilanes of the formula $$R_a SiX_{4-a} \quad (II)$$

in which a, R and X have the meaning given in Formula I. In it, in the presence of at least $10^{-5}$ wt.-% of a catalyst according to the invention, the equilibration mixture is produced in situ by partial esterification with alcohols of the general formula R'OH by a method known in itself, with the evolution of gaseous hydrogen chloride. For this purpose, the chlorosilane, in the presence of an inert solvent if desired, is placed in the reactor in mixture with the catalyst, and the alcohol R'OH is dosed into it in the amount corresponding to the R'O:X ratio desired in the end product I, while heating to drive out the gaseous hydrogen chloride. The reaction mixture obtained is worked up by refluxing until a constant boiling point is reached, maintained at ebullition, and then purified by distillation.

Catalysts suitable according to the invention are especially triphenylphosphine and triphenylphosphine oxide; also suitable, however, are phosphorus nitrile dichloride, diethyl phosphite, and aryl and alkyl phosphonic acid alkyl esters whose ester components have preferably 1 to 4 carbon atoms, and whose alkyl groups are preferably those with 1 to 10 carbon atoms; for example, phenylphosphonic acid diethyl ester, butylphosphonic acid diethyl ester and octylphosphonacid diethyl ester have good catalytic activity and do not interfere with purification by distillation.

As a rule the method according to the invention sets out from chlorosilanes of the general formula II as the one component. These starting products include, for example, tetrachlorosilane, trichlorosilane, methyltrichlorosilane, ethyltrichlorosilane, propyltrichlorosilane, isobutyltrichlorosilane, 4-methylpentyltrichlorosilane, 2,5-dimethylhexyltrichlorosilane, cyclohexyltrichlorosilane, vinyltrichlorosilane, allyltrichlorosilane, 3-chloropropyltrichlorosilane, 2-phenylethyltrichlorosilane, phenyltrichlorosilane, p-bromophenyltrichlorosilane, dichlorodihydrogensilane, methyldichlorohydrogensilane, dimethyldichlorosilane, methylisobutyldichlorosilane, vinylmethyldichlorosilane, chloromethylmethyldichlorosilane, phenylmethyldichlorosilane, diphenyldichlorosilane, etc.

As the second reaction component together with a chlorosilane of the general formula II, as described above, in addition to the more highly esterified halogen partial esters, silane esters of the general formula $$R_a Si(OR')_{4-a}$$

are used, in which R, R' and a have the meaning given in Formula I. Suitable silane esters of this formula are, for example, the halide-free methyl, ethyl, n- and isopropyl, n-, iso- and secondary-butyl, 1-methoxyisopropyl and 2-ethylhexylester derivatives of the above chlorosilanes.

Also usable as starting products are the partial esters of general formula I, listed above as products. Particularly suitable are partial ester chloride mixtures as commonly formed, according to the present state of knowledge, in the known method of the partial esterification of the above chlorosilanes of general formula I with alcohols. However, the degree of esterification of one of the starting products must be higher than the degree of esterification of the desired end products.

The moieties R in the two starting products used should be if possible the same, especially if homogeneous partial esters are desired. It is also possible, however, to use starting products having different alkyl groups. In these cases too, the equilibration takes place in the sense of the present invention. A mixture of the halogen silane esters is obtained with the same degree of esterificaton, which can then be separated by distillation, if desired, into its components.

In another embodiment of the partial esterification of the above chlorosilanes of the general formula I in the presence of the catalysts according to the invention, the alcoholic components are, for example, methanol, ethanol, and isopropanol, n-, iso- and sec-butanol, 1-methoxypropanol-2, 2-ethylhexanol etc. Inert media suitable for use are aliphatic, aromatic and/or chlorinated hydrocarbons. In detail these are, for example, pentanes, hexanes and heptanes, isooctane, cyclohexane, methylcyclohexane, benzine fractions such as petroleum ether or ligroin, benzene, toluene, the xylenols, methylene chloride, chloroform, carbon tetrachloride, trans-dichloroethylene, trichloroethylene, perchloroethylene, chlorobenzene, the dichlorobenzenes, the trichloroethanes, trichlorotrifluoroethane, 1,1,1,3-tetrachloropropane, etc.

The compounds of general formula I find technical application as starting products, for example for the preparation of neutral silicon crosslinking agents in cold-setting, permanently elastic sealing compositions, and for the preparation of phase and boundary surface agents in hydraulic pressure transmission, and in compositions containing isocyanate groups and/or urethane.

The following examples will explain the method without limiting its scope.

EXAMPLE 1

In a four-liter columnar vessel, 2.4 kg (16 mol) of methyltrichlorosilane and 1.42 kg (8 mol) of methyltriethoxysilane were uniformly mixed with 1 gram of triphenylphosphine and stirred for 14 hours at 80° C. Then a column distillation produced a yield of 3.52 kg (approx. 92%) of methylethoxydichlorosilane (b.p.

100.5° C.). Still another product was contained in the hold-up of the distillation vessel.

EXAMPLE 2

In a manner similar to example 1, 3.56 kg of methylethoxydichlorosilane was produced from 1.8 kg (12 mol) of methyltrichlorosilane and 2.16 kg (12 mol) of methyldiethoxychlorosilane with 1 g of isobutylphosphonic acid diethyl ester as catalyst (yield about 93%).

EXAMPLE 3

The reaction apparatus consisted of a heated 4-liter multiple-neck flask with stirrer, internal thermometers, reflux condenser with deep freezer attached for the removal of hydrogen chloride, and a dropping funnel whose neck was immersed in the reaction liquid. 3 kg (28 mol) of methyltrichlorosilane containing 500 mg of triphenyl phosphine oxide in solution was placed in the flask. Over a period of 130 minutes, with stirring, and at ambient temperature, 920 g (20 mol) of anhydrous ethanol was dosed in at a uniform rate, while the internal temperature dropped to +4° C. and a strong evolution of hydrogen chloride took place. Then the reaction mixture was heated for 4 hours at constant ebullition at about 100° C., driving off residual hydrogen chloride, and the mixture was refluxed for an additional 6 hours. Distillation yielded 2.96 kg (approx. 93%) of methyl ethoxy dichlorosilane.

EXAMPLE 4

In a manner similar to Example 1, 2,880 kg of vinyl di-(1-methoxyisopropoxy)chlorosilane, b.p. 82 ° C. (1 mbar) was prepared from 650 g (4 mol) of vinyl trichlorosilane and 2,580 g (8 mol) of vinyl tri-(1-methoxyisopropoxy)silane with 2 g of octylphosphonic acid diethyl ester as catalyst (yield approximately 89%).

EXAMPLE 5

In a manner similar to Example 1, 2,130 grams of tri-secbutoxychlorosilane, b.p. 86° C. (18 mbar) were prepared from 340 g (2 mol) of tetrachlorosilane and 1923 g (6 mol) of tetra-sec-butoxysilane within 20 hours at 160° C. (yield approximate 94%).

EXAMPLE 6

In a manner similar to Example 3, 2190 g of isobutyldiisopropoxychlorosilane, b.p. 67° C. (2 mbar) was prepared from 1916 g (10 mol) of isobutyltrichlorosilane and 1.2 kg (20 mol) of isopropanol in the presence of 700 ml of heptane and 12 hours of final refluxing (yield approx. 92%).

EXAMPLE 7

In a manner similar to Example 1, 1612 g of chloromethylmethylethoxychlorosilane, b.p. 36° C. (5 mbar) (yield approx. 93%), and 1722 g of phenylmethylethoxychlorosilane, b.p. 81° C. (1 mbar) (yield approx. 86%), were prepared in a 6-liter flask from 1910 g (10 mol) of phenylmethyldichlorosilane and 1830 g (10 mol) of chloromethylmethyldiethoxysilane, followed by workup by column distillation in vacuo.

It will be understood that the specification and examples are illustrative but not limitative of the present invention and that other embodiments within the spirit and scope of the invention will suggest themselves to those skilled in the art.

We claim:

1. A method for the production of an organosilicic ester of the formula

$$R_a SiX_n(OR')_{4-a-n} \qquad I$$

wherein X is a halide moiety and n=1 to 3; (OR') is an alkoxy group, and (4−a−n)≧1; R' consists in each case of a saturated and/or unsaturated and/or branched alkyl group having 1 to 8 carbon atoms, a=0, 1 or 2 and the sum of a +n is 1, 2 or a maximum of 3; R is hydrogen, alkyl groups, halogen substituted alkyl groups, alkenyl groups and/or aryl groups substituted with halogen and/or alkyl and a is as above, comprising: effecting equilibration of starting products as a reaction mixture in the presence of a catalyst which is an organic phosphorus compound selected from the group consisting of triphenylphosphine oxide, phosphorus nitrile dichloride, diethyl phosphite, and aryl and alkyl phosphonic acid alkyl esters, said starting products being chlorosilanes and/or partial ester halides with a lower degree of esterification than the desired product, or silane esters and/or partial ester halides whose degree of esterification is higher than that of the desired product.

2. The method of claim 1 wherein R' contains an ether oxygen function.

3. The method of claim 1, wherein the preparation of at least one of the starting products and the equilibration take place simultaneously.

4. The method of claim 3, wherein the chlorosilanes are esterified in the presence of organic phosphorus compounds with an amount of alcohol that corresponds to the desired halogen partial ester.

5. The method of claim 1, wherein the reaction is in an inert solvent.

6. The method of claim 1, conducted at room temperature.

7. The method of claim 1 conducted at an elevated temperature not to exceed the reaction mixture's boiling point.

8. The method of claim 5 wherein the inert solvent is selected from the group consisting of pentanes, hexanes, heptanes, isooctane, cyclohexane, methylcyclohexane, benzine fractions such as petroleum ether or ligroin, benzene, toluene, the xylenols, methylene chloride, chloroform, carbon tetrachloride, trans-dichloroethylene, trichloroethylene, perchloroethylene, chlorobenzene, the dichlorobenzenes, the trichloroethanes, trichlorotrifluroethane, and 1,1,1,3-tetrachloropropane.

9. The method of claim 4 wherein the alcohol is selected from the group consisting of methanol, ethanol, n- and isopropanol, n-, iso- and sec-butanol, 1-methoxypropanol-2, and 2-ethylhexanol.

10. The method of claim 1 wherein the phosphoric acid alkyl ester has 1 to 4 carbon atoms in the ester group.

11. The method of claim 1 wherein the alkyl phosphoric acid alkyl ester has 1 to 10 carbon atoms in the alkyl group.

12. The method of claim 1 wherein the starting products are methyltriethoxysilane and methyltrichlorosilane.

13. The method of claim 1 wherein the starting products are methyltrichlorisilane and methyldiethoxychlorosilane.

14. The method of claim 1 wherein the starting products are vinyltrichlorosilane and vinyl tri-(1-methoxyisopropoxy) silane.

15. The method of claim 1 wherein the starting products are tetrachlorosilane and tetra-sec-butoxysilane.

16. The method of claim 4 wherein the chlorosilane is methyltrichlorosilane and the alcohol is ethanol.

17. The method of claim 4 wherein the chlorosilane is isobutytrichlorosilane and the alcohol is isopropanol.

18. The method of claim 1 wherein the catalyst is isobutyphosphonic acid diethyl ester.

19. The method of claim 1 wherein the catalyst is octylphosphonic acid diethyl ester.

* * * * *